US010689336B2

(12) United States Patent
Bando et al.

(10) Patent No.: US 10,689,336 B2
(45) Date of Patent: Jun. 23, 2020

(54) RADICAL POLYMERIZATION INITIATOR AND METHOD FOR PRODUCING POLYMERS

(71) Applicants: KYOTO UNIVERSITY, Kyoto-shi, Kyoto (JP); ZEON CORPORATION, Tokyo (JP)

(72) Inventors: Fumiaki Bando, Tokyo (JP); Shigeru Yamago, Kyoto (JP)

(73) Assignees: ZEON CORPORATION, Tokyo (JP); KYOTO UNIVERSITY, Kyoto-shi (JP)

(*) Notice: Subject to any disclaimer, the term of this patent is extended or adjusted under 35 U.S.C. 154(b) by 0 days.

(21) Appl. No.: 16/439,109

(22) Filed: Jun. 12, 2019

(65) Prior Publication Data

US 2019/0292146 A1 Sep. 26, 2019

Related U.S. Application Data

(62) Division of application No. 15/038,579, filed as application No. PCT/JP2014/081334 on Nov. 27, 2014, now abandoned.

(30) Foreign Application Priority Data

Nov. 27, 2013 (JP) ................... 2013-245352

(51) Int. Cl.
| | |
|---|---|
| *C08F 2/48* | (2006.01) |
| *C08F 4/04* | (2006.01) |
| *C07C 395/00* | (2006.01) |
| *C08F 4/00* | (2006.01) |
| *C08F 12/08* | (2006.01) |
| *C08F 236/08* | (2006.01) |
| *C08F 112/08* | (2006.01) |
| *C08F 120/34* | (2006.01) |
| *C08F 212/08* | (2006.01) |
| *C08F 220/12* | (2006.01) |
| *C08F 220/14* | (2006.01) |
| *C08F 220/44* | (2006.01) |
| *C08F 236/12* | (2006.01) |
| *C08F 299/00* | (2006.01) |

(52) U.S. Cl.
CPC .............. *C07C 395/00* (2013.01); *C08F 2/48* (2013.01); *C08F 4/00* (2013.01); *C08F 4/04* (2013.01); *C08F 12/08* (2013.01); *C08F 112/08* (2013.01); *C08F 120/34* (2013.01); *C08F 212/08* (2013.01); *C08F 220/12* (2013.01); *C08F 220/14* (2013.01); *C08F 220/44* (2013.01); *C08F 236/08* (2013.01); *C08F 236/12* (2013.01); *C08F 299/00* (2013.01)

(58) Field of Classification Search
None
See application file for complete search history.

(56) References Cited

U.S. PATENT DOCUMENTS

| | | | |
|---|---|---|---|
| 5,043,477 A | 8/1991 | Higa et al. | |
| 6,274,688 B1 * | 8/2001 | Nakagawa | C08F 2/38 526/328 |
| 2005/0271978 A1 | 12/2005 | Takeda et al. | |
| 2006/0052563 A1 | 3/2006 | Nakagawa et al. | |
| 2006/0167199 A1 | 7/2006 | Yamago et al. | |
| 2010/0016191 A1 | 1/2010 | Harrison et al. | |

FOREIGN PATENT DOCUMENTS

| | | |
|---|---|---|
| CN | 102344537 A | 2/2012 |
| JP | 2004-323693 A | 11/2004 |
| JP | 2005-344009 A | 12/2005 |
| JP | 2007-254758 A | 10/2007 |
| JP | 2007-277533 A | 10/2007 |
| JP | 2012-236984 A | 12/2012 |
| JP | 2012236984 A * | 12/2012 |
| WO | 2004/014962 A1 | 2/2004 |

OTHER PUBLICATIONS

Computer-generated English-language translation of JP-2012236984-A. (Year: 2012).*
International Search Report dated Mar. 10, 2015, issued in counterpart International Application No. PCT/JP2014/081334 (1 page).
Yoshiki Nakagawa et al., "Synthesis of Well-Defined Allyl End-Functionalized Polystyrene by Atom Transfer Radical Polymerization with an Allyl Halide Initiator", Polymer Journal, 1998, vol. 30, No. 2, pp. 138-141.
Office Action dated Jan. 18, 2017, issued in Chinese Patent Application No. 201480063079.0 (6 pages).
Yamago et al, "Experimental and theoretical studies on formal σ-bond metathesis of silyl tellurides with alkyl halides", Journal of Organometalic Chemistry, 2007, pp. 664-670, vol. 692; cited in Chinese Office Action dated Jan. 18, 2017 (7 pages).

(Continued)

*Primary Examiner* — Vu A Nguyen
(74) *Attorney, Agent, or Firm* — Westerman, Hattori, Daniels & Adrian, LLP

(57) ABSTRACT

The present invention involves a radical polymerization initiator comprising an organotellurium compound represented by a formula (1), wherein $R^1$ represents an alkyl group or the like, each of $R^2$ and $R^3$ independently represents a hydrogen atom or the like, and each of $R^4$, $R^5$, and $R^6$ independently represents a hydrogen atom or the like. The present invention provides: a radical polymerization initiator that is useful for producing a polymer that includes a double bond at the molecular terminal; and a method for producing a polymer that utilizes the radical polymerization initiator.

(1)

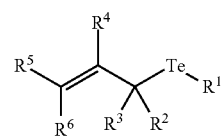

5 Claims, No Drawings

(56) References Cited

OTHER PUBLICATIONS

Higa et al, "Synthesis and Characterization of Diallyl Telluride and Allyl Methil Telluride", Organometallics, 1989, pp. 1674-1678, vol. 8; cited in Chinese Office Action dated Jan. 18, 2017 (4 pages).

Extended European Search Report dated May 15, 2017, issued in European Patent Application No. 14866248.9.

Comasseto et al., "Alkaline Hydrolysis of Diaryl Ditelludides Under Phase Transfer Conditions; Synthesis of Alkyl Aryl Tellurides", Journal of Organometallic Chemistry, 1984, pp. 261-266.

Russavskaya et al., "Reaction of 1-Bromo-3-chloropropane with Tellur and Dimethyltelluride in the System of Hydrazine Hydrate-Alkali", Russian Journal of General Chemistry, 2006, pp. 726-729, vol. 76 No. 5.

Vojtova et al., Mat. Res. Soc. Symp. Proc.vol. 774, 2003, O1.8.1-O1.8.15.

"Vinyl Polymers", downloaded from http://pslc.ws/macrog/vinyl.htm (Year: 2018).

Fonagy et al., Macromolecules 2007, 40, 1401-1407.

\* cited by examiner

RADICAL POLYMERIZATION INITIATOR AND METHOD FOR PRODUCING POLYMERS

CROSS-REFERENCE TO RELATED APPLICATIONS

This is a divisional of U.S. application Ser. No. 15/038,579 filed on May 23, 2016, which is a 371 of PCT/JP2014/081334 filed on Nov. 27, 2014 which claims foreign priority to Japanese Application No. 2013-245352 filed on Nov. 27, 2013, the entire contents of which is incorporated herein by reference.

TECHNICAL FIELD

The present invention relates to a radical polymerization initiator that is useful for producing a polymer that includes a double bond at the molecular terminal, and a method for producing a polymer that utilizes the radical polymerization initiator.

BACKGROUND ART

A polymer that includes a double bond at the molecular terminal is used as a macromonomer when producing a polymer that has a branched structure (e.g., graft polymer or star-shaped polymer).

For example, Patent Literature 1 discloses a method for producing a polymer having a branched structure wherein a macromonomer is polymerized, the macromonomer including a group that includes a polymerizable carbon-carbon double bond at the molecular terminal. Patent Literature 1 discloses a method for producing a macromonomer wherein a vinyl-based monomer is polymerized using an atom transfer radical polymerization method that utilizes a polymerization initiator (e.g., organic halide) and a catalyst (e.g., transition metal complex) to obtain a vinyl-based polymer that includes a terminal halogen group, and the terminal halogen group is substituted with a compound that includes a double bond, for example.

When using the method disclosed in Patent Literature 1 wherein a functional group (e.g., halogen group) situated at the molecular terminal is substituted with a group that includes a carbon-carbon double bond, it is necessary to effect a functional group substitution reaction. Therefore, a method that introduces a carbon-carbon double bond into the polymerization-initiation terminal using a polymerization initiator that includes a carbon-carbon double bond has been studied in order to more easily obtain a macromonomer. Examples of such a method include an atom transfer radical polymerization method that utilizes an allyl halide as a polymerization initiator (see Non-Patent Literature 1). However, the type of vinyl-based monomer that can be applied to the atom transfer radical polymerization method that utilizes an allyl halide as a polymerization initiator is limited. Moreover, it may be difficult to control the polymerization reaction, or the polymerization reaction may not proceed depending on the type of vinyl-based monomer. In view of the above situation, a radical polymerization initiator that includes a carbon-carbon double bond, and can be applied to a wide variety of radically polymerizable monomers (e.g., vinyl-based monomer) to implement a controlled polymerization reaction, has been strongly desired.

However, since a radical polymerization initiator has reactivity with a carbon-carbon double bond, a radical polymerization initiator normally does not exhibit sufficient polymerization activity when a carbon-carbon double bond is introduced into the molecule of the radical polymerization initiator. Specifically, a radical polymerization initiator that includes a carbon-carbon double bond and has the desired properties has not yet been obtained.

An organotellurium compound is known as a radical polymerization initiator that makes it possible to subject a vinyl-based monomer or the like to radical polymerization while controlling the molecular weight distribution and the like (see Patent Literature 2 and 3).

CITATION LIST

Patent Literature

Patent Literature 1: JP-A-2007-254758 (US2006/0052563A)

Patent Literature 2: WO2004/014962 (US2006/0167199A)

Patent Literature 3: JP-A-2007-277533

Non-Patent Literature

Non-Patent Literature 1: Yoshiki Nakagawa and Krzysztof Matyjaszewski, "Synthesis of Well-Defined Allyl End-Functionalized Polystyrene by Atom Transfer Radical Polymerization with an Allyl Halide Initiator", Polymer Journal, 1998, Vol. 30, No. 2, pp. 138-141

SUMMARY OF INVENTION

Technical Problem

The invention was conceived in view of the above situation. An object of the invention is to provide a radical polymerization initiator that is useful for producing a polymer that includes a double bond at the molecular terminal, and can be applied to a wide variety of radically polymerizable monomers to implement a controlled polymerization reaction, and a method for producing a polymer that utilizes the radical polymerization initiator.

Solution to Problem

The inventors conducted extensive studies with regard to a radical polymerization initiator that is used for a living radical polymerization reaction in order to solve the above problem. As a result, the inventors found that a wide variety of radically polymerizable monomers can be polymerized in a controlled manner, and a polymer that includes a double bond at the molecular terminal can be efficiently obtained by subjecting a radically polymerizable monomer to a living radical polymerization reaction in the presence of a radical polymerization initiator that includes an organotellurium compound that includes at least one non-aromatic carbon-carbon double bond at the β-position. This finding has led to the completion of the invention.

Several aspects of the invention provide the following radical polymerization initiator (see (1)), method for producing a polymer (see (2) to (5)), and polymer (see (6)).

(1) A radical polymerization initiator including an organotellurium compound represented by the following formula (1),

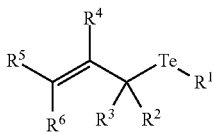

(1)

wherein $R^1$ represents a group selected from an alkyl group, a substituted or unsubstituted cycloalkyl group, a substituted or unsubstituted aryl group, and a substituted or unsubstituted heteroaromatic ring group, each of $R^2$ and $R^3$ independently represents an atom or a group selected from a hydrogen atom, an aliphatic hydrocarbon group, a substituted or unsubstituted aryl group, a substituted or unsubstituted heteroaromatic ring group, a halogen atom, a carboxyl group, a hydrocarbyloxycarbonyl group, a cyano group, and an amide group, and each of $R^4$, $R^5$, and $R^6$ independently represents an atom or a group selected from a hydrogen atom, an aliphatic hydrocarbon group, a substituted or unsubstituted aryl group, a substituted or unsubstituted heteroaromatic ring group, a halogen atom, a carboxyl group, a hydrocarbyloxycarbonyl group, a cyano group, an amide group, and a group represented by the following formula (2), provided that two groups selected from $R^2$ to $R^6$ are optionally bonded to each other to form a ring other than an aromatic ring,

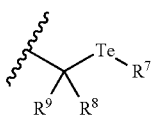

(2)

wherein $R^7$ represents a group selected from an alkyl group, a substituted or unsubstituted cycloalkyl group, a substituted or unsubstituted aryl group, and a substituted or unsubstituted heteroaromatic ring group, each of $R^8$ and $R^9$ independently represents an atom or a group selected from a hydrogen atom, an aliphatic hydrocarbon group, a substituted or unsubstituted aryl group, a substituted or unsubstituted heteroaromatic ring group, a halogen atom, a carboxyl group, a hydrocarbyloxycarbonyl group, a cyano group, and an amide group, and the wavy line represents that the group represented by the formula (2) is bonded to the carbon atom included in the formula (1) that forms the double bond.

(2) A method for producing a polymer including subjecting a radically polymerizable monomer to radical polymerization in a state in which the radical polymerization initiator according to (1) is present in a polymerization system.

(3) The method for producing a polymer according to (2), wherein the radically polymerizable monomer is subjected to radical polymerization in a state in which an azo-based radical generator is further present in the polymerization system.

(4) The method for producing a polymer according to (2) or (3), wherein the radically polymerizable monomer is subjected to radical polymerization in a state in which light is applied to the polymerization system.

(5) The method for producing a polymer according to any one of (2) to (4), wherein the radically polymerizable monomer is subjected to radical polymerization in a state in which a ditelluride compound represented by the following formula (3) is further present in the polymerization system, $$R^{10}Te\text{-}TeR^{11}$$ (3)

wherein each of $R^{10}$ and $R^{11}$ independently represents a group selected from an alkyl group, a substituted or unsubstituted cycloalkyl group, a substituted or unsubstituted aryl group, and a substituted or unsubstituted heteroaromatic ring group.

(6) A polymer obtained by the method for producing a polymer according to any one of (2) to (5).

Advantageous Effects of Invention

The aspects of the invention thus provide a radical polymerization initiator that is useful for producing a polymer that includes a double bond at the molecular terminal, and can be applied to a wide variety of radically polymerizable monomers to implement a controlled polymerization reaction, and a method for producing a polymer that utilizes the radical polymerization initiator.

Note that the expression "includes a double bond at the molecular terminal" used herein means that a group represented by $(R^5)(R^6)C=C(R^4)-C(R^2)(R^3)-$ that is derived from the organotellurium compound represented by the formula (1) forms one of the terminals of the polymer chain.

DESCRIPTION OF EMBODIMENTS

A radical polymerization initiator and a method for producing a polymer according to the exemplary embodiments of the invention are described in detail below.

1) Radical Polymerization Initiator

A radical polymerization initiator according to one embodiment of the invention includes the organotellurium compound represented by the formula (1).

$R^1$ in the formula (1) represents a group selected from an alkyl group, a substituted or unsubstituted cycloalkyl group, a substituted or unsubstituted aryl group, and a substituted or unsubstituted heteroaromatic ring group. Among these, an alkyl group and a substituted or unsubstituted aryl group are preferable as $R^1$.

Note that the expression "substituted or unsubstituted" used herein in connection with a group or the like means that the group or the like is unsubstituted, or substituted with a substituent.

The number of carbon atoms of the alkyl group that may be represented by $R^1$ is not particularly limited, but is preferably 1 to 10, more preferably 1 to 8, and still more preferably 1 to 5, from the viewpoint of availability.

Examples of the alkyl group that may be represented by $R^1$ include a linear alkyl group such as a methyl group, an ethyl group, an n-propyl group, an n-butyl group, an n-pentyl group, an n-hexyl group, an n-heptyl group, an n-octyl group, an n-nonyl group, and an n-decyl group; and a branched alkyl group such as an isopropyl group, a sec-butyl group, and a tert-butyl group.

The number of carbon atoms of the cycloalkyl group (that is substituted or unsubstituted) that may be represented by $R^1$ is normally 3 to 10. The number of carbon atoms of the cycloalkyl group is preferably 3 to 8, and more preferably 5 or 6, from the viewpoint of availability.

Examples of the cycloalkyl group (that is substituted or unsubstituted) that may be represented by $R^1$ include a cyclopropyl group, a cyclobutyl group, a cyclopentyl group, a cyclohexyl group, a cycloheptyl group, a cyclooctyl group, and the like.

A substituent that may substitute the cycloalkyl group (that is substituted or unsubstituted) that may be represented by $R^1$ is not particularly limited as long as the substituent does not hinder the polymerization reaction. Examples of the substituent include a halogen atom such as a fluorine atom, a chlorine atom, a bromine atom, and an iodine atom; a hydroxyl group; an alkyl group having 1 to 8 carbon atoms, such as a methyl group, an ethyl group, an n-propyl group, and an isopropyl group; an alkoxy group having 1 to 8 carbon atoms, such as a methoxy group and an ethoxy group; an amino group; a nitro group; a cyano group; a group represented by —CORa (wherein Ra represents an alkyl group having 1 to 8 carbon atoms, such as a methyl group, an ethyl group, an n-propyl group, and an isopropyl group; a cycloalkyl group having 3 to 8 carbon atoms, such as a cyclopropyl group, a cyclobutyl group, and a cyclopentyl group; an aryl group having 6 to 10 carbon atoms, such as a phenyl group, a 1-naphthyl group, and a 2-naphthyl group; an alkoxy group having 1 to 8 carbon atoms, such as a methoxy group and an ethoxy group; a substituted or unsubstituted aryloxy group having 6 to 10 carbon atoms, such as a phenoxy group and a 2,4,6-trimethylphenyloxy group; and a haloalkyl group having 1 to 8 carbon atoms, such as a trifluoromethyl group; and the like.

The number of carbon atoms of the aryl group (that is substituted or unsubstituted) that may be represented by $R^1$ is normally 6 to 20. The number of carbon atoms of the aryl group is preferably 6 to 15, and more preferably 6 to 10, from the viewpoint of availability.

Examples of the aryl group (that is substituted or unsubstituted) include a phenyl group, a 1-naphthyl group, a 2-naphthyl group, an anthranyl group, and the like.

A substituent that may substitute the aryl group (that is substituted or unsubstituted) is not particularly limited as long as the substituent does not hinder the polymerization reaction. Examples of the substituent include those mentioned above in connection with the cycloalkyl group (that is substituted or unsubstituted).

The number of carbon atoms of the heteroaromatic ring group (that is substituted or unsubstituted) that may be represented by $R^1$ is normally 1 to 15. The number of carbon atoms of the heteroaromatic ring group is preferably 3 to 15, and more preferably 4 to 10, from the viewpoint of availability.

Examples of the heteroaromatic ring group (that is substituted or unsubstituted) include a 5-membered heteroaromatic ring group such as a pyrrolyl group, an imidazolyl group, a furyl group, a thienyl group, an oxazolyl group, and a thiazolyl group; a 6-membered heteroaromatic ring group such as a pyridyl group, a pyrimidyl group, a pyridazyl group, and a pyrazinyl group; a fused heteroaromatic ring group such as a benzimidazolyl group, a quinolyl group, and a benzofuranyl group; and the like.

A substituent that may substitute the heteroaromatic ring group (that is substituted or unsubstituted) is not particularly limited as long as the substituent does not hinder the polymerization reaction. Examples of the substituent include those mentioned above in connection with the cycloalkyl group (that is substituted or unsubstituted).

Each of $R^2$ and $R^3$ in the formula (1) independently represents an atom or a group selected from a hydrogen atom, an aliphatic hydrocarbon group, a substituted or unsubstituted aryl group, a substituted or unsubstituted heteroaromatic ring group, a halogen atom, a carboxyl group, a hydrocarbyloxycarbonyl group, a cyano group, and an amide group. Among these, a hydrogen atom and an aliphatic hydrocarbon group are preferable as $R^2$ and $R^3$.

The number of carbon atoms of the aliphatic hydrocarbon group that may be represented by $R^2$ and $R^3$ is preferably 1 to 10, more preferably 1 to 8, and still more preferably 1 to 5.

Examples of the aliphatic hydrocarbon group that may be represented by $R^2$ and $R^3$ include an alkyl group having 1 to 10 carbon atoms, such as a methyl group and an ethyl group; an alkenyl group having 2 to 10 carbon atoms, such as a 1-propenyl group and a 2-propenyl group; an alkynyl group having 2 to 10 carbon atoms, such as a 1-propynyl group and a 2-propynyl group; a cycloalkyl group having 3 to 10 carbon atoms, such as a cyclopropyl group, a cyclobutyl group, a cyclopentyl group, and a cyclohexyl group; and the like.

Specific examples of the substituted or unsubstituted aryl group that may be represented by $R^2$ and $R^3$ include those mentioned above in connection with the substituted or unsubstituted aryl group that may be represented by $R^1$.

Specific examples of the substituted or unsubstituted heteroaromatic ring group that may be represented by $R^2$ and $R^3$ include those mentioned above in connection with the substituted or unsubstituted heteroaromatic ring group that may be represented by $R^1$.

Examples of the halogen atom that may be represented by $R^2$ and $R^3$ include a fluorine atom, a chlorine atom, a bromine atom, an iodine atom, and the like.

The number of carbon atoms of the hydrocarbyloxycarbonyl group that may be represented by $R^2$ and $R^3$ is preferably 2 to 10, more preferably 2 to 8, and still more preferably 2 to 5.

Examples of the hydrocarbyloxycarbonyl group that may be represented by $R^2$ and $R^3$ include an alkyloxycarbonyl group such as a methyloxycarbonyl group and an ethyloxycarbonyl group; an alkenyloxycarbonyl group such as an ethenyloxycarbonyl group and a 2-propenyloxycarbonyl group; an alkynyloxycarbonyl group such as a propagyloxycarbonyl group; a substituted or unsubstituted aryloxycarbonyl group such as a phenoxycarbonyl group, a 4-methylphenyloxycarbonyl group, a 4-chlorophenoxycarbonyl group, a 1-naphthyloxycarbonyl group, and a 2-naphthyloxycarbonyl group; and the like.

Examples of the amide group that may be represented by $R^2$ and $R^3$ include a group represented by —C(X)—N($r^1$)($r^2$) (wherein X represents an oxygen atom, a sulfur atom, or a selenium atom, and each of $r^1$ and $r^2$ independently represents a hydrogen atom or an organic group having 1 to 10 carbon atoms), a group represented by —SO$_2$—N($r^1$)($r^2$) (wherein $r^1$ and $r^2$ are the same as defined above), and a group represented by —N($r^1$)-C(O)-($r^2$) (wherein $r^1$ and $r^2$ are the same as defined above).

Examples of the organic group that may be represented by $r^1$ and $r^2$ include a linear or branched alkyl group having 1 to 10 carbon atoms, such as a methyl group and an ethyl group; a linear or branched alkenyl group having 2 to 10 carbon atoms, such as a 1-propenyl group and a 2-propenyl group; a linear or branched alkynyl group having 2 to 10 carbon atoms, such as a 1-propynyl group and a 2-propynyl group; a cycloalkyl group having 3 to 10 carbon atoms, such as a cyclopropyl group, a cyclobutyl group, a cyclopentyl group, and a cyclohexyl group; an aryl group having 6 to 10 carbon atoms, such as a phenyl group and a 1-naphthyl group; an alkylcarbonyl group having 2 to 10 carbon atoms, such as an acetyl group; an alkoxycarbonyl group having 2 to 10 carbon atoms, such as a methoxycarbonyl group; a hydrocarbylsulfonyl group having 1 to 10 carbon atoms, such as a methylsulfonyl group and a p-toluenesulfonyl group; and the like.

Examples of the group represented by —C(X)—N($r^1$)($r^2$) include an aminocarbonyl group, a methylaminocarbonyl group, an ethylaminocarbonyl group, a benzylaminocarbonyl group, a phenylaminocarbonyl group, a dimethylaminocarbonyl group, a phenylmethylaminocarbonyl group, a dimethylaminothiocarbonyl group, a dimethylaminoselenocarbonyl group, and the like.

Examples of the group represented by —$SO_2$—$N(r^1)(r^2)$ include an aminosulfonyl group, a methylaminosulfonyl group, a benzylaminosulfonyl group, a dimethylaminosulfonyl group, and the like.

Examples of the group represented by —$N(r^1)$-C(O)-$(r^2)$ include an acetylamino group, a benzoylamino group, and the like.

Each of $R^4$, $R^5$, and $R^6$ in the formula (1) independently represents an atom or a group selected from a hydrogen atom, an aliphatic hydrocarbon group, a substituted or unsubstituted aryl group, a substituted or unsubstituted heteroaromatic ring group, a halogen atom, a carboxyl group, a hydrocarbyloxycarbonyl group, a cyano group, an amide group, and a group represented by the formula (2). Among these, a hydrogen atom, an aliphatic hydrocarbon group (including a ring that is formed by $R^4$ and $R^5$ that are bonded to each other), a hydrocarbyloxycarbonyl group, and the group represented by the formula (2) are preferable as $R^4$, $R^5$, and $R^6$.

Specific examples of the aliphatic hydrocarbon group that may be represented by $R^4$, $R^5$, and $R^6$ include those mentioned above in connection with the aliphatic hydrocarbon group that may be represented by $R^2$ and $R^3$.

Specific examples of the substituted or unsubstituted aryl group that may be represented by $R^4$, $R^5$, and $R^6$ include those mentioned above in connection with the substituted or unsubstituted aryl group that may be represented by $R^1$.

Specific examples of the substituted or unsubstituted heteroaromatic ring group that may be represented by $R^4$, $R^5$, and $R^6$ include those mentioned above in connection with the substituted or unsubstituted heteroaromatic ring group that may be represented by $R^1$.

Specific examples of the halogen atom that may be represented by $R^4$, $R^5$, and $R^6$ include those mentioned above in connection with the halogen atom that may be represented by $R^2$ and $R^3$.

Specific examples of the hydrocarbyloxycarbonyl group that may be represented by $R^4$, $R^5$, and $R^6$ include those mentioned above in connection with the hydrocarbyloxycarbonyl group that may be represented by $R^2$ and $R^3$.

Specific examples of the amide group that may be represented by $R^4$, $R^5$, and $R^6$ include those mentioned above in connection with the amide group that may be represented by $R^2$ and $R^3$.

$R^7$ in the formula (2) represents a group selected from an alkyl group, a substituted or unsubstituted cycloalkyl group, a substituted or unsubstituted aryl group, and a substituted or unsubstituted heteroaromatic ring group. Among these, an alkyl group and a substituted or unsubstituted aryl group are preferable as $R^7$.

Specific examples of the alkyl group, the substituted or unsubstituted cycloalkyl group, the substituted or unsubstituted aryl group, and the substituted or unsubstituted heteroaromatic ring group that may be represented by $R^7$ include those mentioned above in connection with the alkyl group, the substituted or unsubstituted cycloalkyl group, the substituted or unsubstituted aryl group, and the substituted or unsubstituted heteroaromatic ring group that may be represented by $R^1$.

Each of $R^8$ and $R^9$ in the formula (2) independently represents an atom or a group selected from a hydrogen atom, an aliphatic hydrocarbon group, a substituted or unsubstituted aryl group, a substituted or unsubstituted heteroaromatic ring group, a halogen atom, a carboxyl group, a hydrocarbyloxycarbonyl group, a cyano group, and an amide group. Among these, a hydrogen atom and an aliphatic hydrocarbon group are preferable as $R^8$ and $R^9$.

Specific examples of the aliphatic hydrocarbon group, the substituted or unsubstituted aryl group, the substituted or unsubstituted heteroaromatic ring group, the halogen atom, the hydrocarbyloxycarbonyl group, and the amide group that may be represented by $R^8$ and $R^9$ include those mentioned above in connection with the aliphatic hydrocarbon group, the substituted or unsubstituted aryl group, the substituted or unsubstituted heteroaromatic ring group, the halogen atom, the hydrocarbyloxycarbonyl group, and the amide group that may be represented by $R^2$ and $R^3$.

Note that two groups selected from $R^2$ to $R^6$ are optionally bonded to each other to form a ring other than an aromatic ring. A hydrocarbon ring is preferable as the ring other than an aromatic ring.

The ring is preferably a 5 to 7-membered ring, and more preferably a 6-membered ring.

Examples of the ring when the ring includes a double bond (e.g., when $R^3$ and $R^6$ or $R^4$ and $R^5$ are bonded to each other), include a substituted or unsubstituted cyclopentene ring, a substituted or unsubstituted cyclohexene ring, a substituted or unsubstituted cycloheptene ring, and the like.

Examples of the ring when the ring does not include a double bond (e.g., when $R^5$ and $R^6$ are bonded to each other), include a substituted or unsubstituted cyclopentane ring, a substituted or unsubstituted cyclohexane ring, a substituted or unsubstituted cycloheptane ring, and the like.

Examples of a substituent that may substitute the ring include those mentioned above in connection with the substituent that may substitute $R^2$ to $R^6$.

Specific examples of the organotellurium compound represented by the formula (1) include 3-methyltellanyl-1-propene, 3-methyltellanyl-2-methyl-1-propene, 3-methyltellanyl-2-phenyl-1-propene, 3-methyltellanyl-3-methyl-1-propene, 3-methyltellanyl-3-phenyl-1-propene, 3-methyltellanyl-3-cyclohexyl-1-propene, 3-methyltellanyl-3-cyano-1-propene, 3-ethyltellanyl-1-propene, 3-methyltellanyl-3-dimethylaminocarbonyl-1-propene, 3-[(n-propyl)tellanyl]-1-propene, 3-isopropyltellanyl-1-propene, 3-(n-butyl)tellanylpropene, 3-[(n-hexyl)tellanyl]-1-propene, 3-phenyltellanyl-1-propene, 3-[(p-methylphenyl)tellanyl]-1-propene, 3-cyclohexyltellanyl-1-propene, 3-[(2-pyridyl)tellanyl]-1-propene, 3-methyltellanyl-2-butene, 3-methyltellanyl-1-cyclopentene, 3-methyltellanyl-1-cyclohexene, 3-methyltellanyl-1-cyclooctene, 3-ethyltellanyl-1-cyclohexene, 3-methyltellanyl-1-cyclohexene, 3-[(n-propyl)tellanyl]-1-cyclohexene, 3-([n-butyl)tellanyl]-1-cyclohexene, methyl 2-(methyltellanylmethyl)acrylate, ethyl 2-(methyltellanylmethyl)acrylate, n-butyl 2-(methyltellanylmethyl)acrylate, methyl 2-(ethyltellanylmethyl)acrylate, methyl 2-([n-butyl)tellanylmethyl]acrylate, methyl 2-(cyclohexyltellanylmethyl)acrylate, 1,4-bis(methyltellanyl)-2-butene, 1,4-bis(ethyltellanyl)-2-butene, 1,4-bis[(n-butyl)tellanyl]-2-butene, 1,4-bis(cyclohexyltellanyl)-2-butene, 1,4-bis(phenyltellanyl)-2-butene, and the like. Note that the organotellurium compound used in connection with one embodiment of the invention is not limited to these organotellurium compounds.

The organotellurium compound represented by the formula (1) may be obtained by reacting a compound represented by the following formula (4), a compound represented by the following formula (5), and metallic tellurium according to the method disclosed in WO2004/014962, for example.

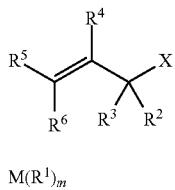

(4)

$M(R^1)_m$ (5)

Note that $R^2$ to $R^6$ in the formula (4) are the same as defined above. X represents a halogen atom. The halogen atom represented by X may be a fluorine atom, a chlorine atom, a bromine atom, or an iodine atom. Among these, a chlorine atom and a bromine atom are preferable.

$R^1$ in the formula (5) is the same as defined above. M represents an alkali metal such as lithium, sodium, or potassium, an alkaline-earth metal such as magnesium or calcium, or copper. m is 1 when M represents an alkali metal, is 2 when M represents an alkaline-earth metal, and is 1 or 2 when M represents copper. When M in the formula (5) represents magnesium, one of the two groups represented by $R^1$ may be a halogen atom. Specifically, the compound represented by the formula (5) may be a Grignard reagent.

More specifically, metallic tellurium is suspended in a solvent in an inert gas atmosphere to prepare a suspension, and the compound represented by the formula (5) is added to the suspension to effect a reaction. The compound represented by the formula (4) is added to the resulting reaction mixture to effect a reaction to obtain the organotellurium compound represented by the formula (1).

The compound represented by the formula (5) is normally used in an amount of 0.5 to 1.5 mol, and preferably 0.8 to 1.2 mol, based on 1 mol of metallic tellurium.

The compound represented by the formula (4) is normally used in an amount of 0.5 to 1.5 mol, and preferably 0.8 to 1.2 mol, based on 1 mol of metallic tellurium.

Examples of the inert gas include nitrogen gas, helium gas, argon gas, and the like.

Examples of the solvent include an ether-based solvent such as diethyl ether and tetrahydrofuran; an amide-based solvent such as dimethylformamide; an aromatic solvent such as toluene; an aliphatic hydrocarbon-based solvent such as hexane; and the like.

Each of the compound represented by the formula (5) and the compound represented by the formula (4) is preferably added dropwise to the reaction system at a low temperature (−20 to 5° C.).

The reaction conditions are not particularly limited. For example, the reaction time is set to 5 minutes to 24 hours, and the reaction temperature is set to −20 to 80° C.

Organotellurium compounds respectively represented by the following formulas (1a) to (1c) may be obtained as follows.

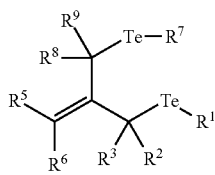

(1a)

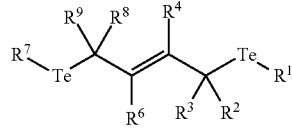

(1b)

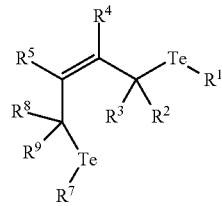

(1c)

wherein $R^1$ to $R^9$ are the same as defined above.

Specifically, the organotellurium compounds respectively represented by the formulas (1a) to (1c) may be obtained by reacting compounds respectively represented by the following formulas (4a) to (4c) as described above instead of the compound represented by the formula (4).

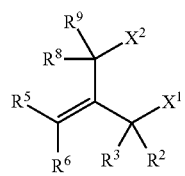

(4a)

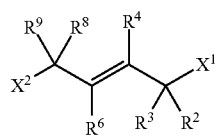

(4b)

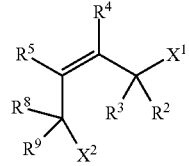

(4c)

wherein $R^2$ to $R^9$ are the same as defined above, provided that $R^4$, $R^5$, and $R^6$ are not the group represented by the formula (2), and $X^1$ and $X^2$ represent a halogen atom (preferably a chlorine atom or a bromine atom).

When using the compounds respectively represented by the formulas (4a) to (4c), the compounds respectively represented by the formulas (4a) to (4c) are normally used in an amount of 0.25 to 0.75 mol, and preferably 0.4 to 0.6 mol, based on 1 mol of metallic tellurium. The compound represented by the formula (5) is normally used in an amount of 0.5 to 1.5 mol, and preferably 0.8 to 1.2 mol, based on 1 mol of metallic tellurium.

After completion of the reaction, the target product may be isolated by a known post-treatment operation and separation-purification means. For example, the reaction mixture is sequentially washed with deaerated water, a deaerated ammonium chloride aqueous solution, and a deaerated saturated sodium chloride solution, and the organic layer is dried and concentrated to obtain a crude product. The resulting reaction product is optionally purified using a known purification method (e.g., vacuum distillation method) to obtain the target organotellurium compound having high purity.

The organotellurium compound represented by the formula (1) that is used as the radical polymerization initiator according to one embodiment of the invention includes at least one non-aromatic carbon-carbon double bond at the β-position with respect to Te.

When a radically polymerizable monomer is subjected to radical polymerization in the presence of the organotellurium compound represented by the formula (1), the carbon-carbon double bond is introduced into the polymerization-initiation terminal, and a living radical polymerization reaction with excellent controllability can be implemented (described later).

Therefore, it is possible to efficiently produce a polymer that includes a double bond at the molecular terminal by utilizing the radical polymerization initiator according to one embodiment of the invention.

2) Method for Producing Polymer

A method for producing a polymer according to one embodiment of the invention includes subjecting a radically polymerizable monomer to radical polymerization in a state in which the radical polymerization initiator according to one embodiment of the invention is present in a polymerization system (i.e., in the presence of the radical polymerization initiator according to one embodiment of the invention).

The radically polymerizable monomer used in connection with one embodiment of the invention is not particularly limited as long as it is radically polymerizable. Examples of the radically polymerizable monomer include an acrylic-based monomer such as methyl (meth)acrylate, ethyl (meth)acrylate, propyl (meth)acrylate, butyl (meth)acrylate, octyl (meth)acrylate, lauryl (meth)acrylate, 2-hydroxyethyl (meth)acrylate, cyclohexyl (meth)acrylate, methylcyclohexyl (meth)acrylate, isobornyl (meth)acrylate, cyclododecyl (meth)acrylate, glycidyl (meth)acrylate, (meth)acrylic acid, (meth)acrylamide, N-methyl(meth)acrylamide, N-isopropyl(meth)acrylamide, N,N-dimethyl(meth)acrylamide, N-(2-dimethylaminoethyl)(meth)acrylamide, N-(3-dimethylaminopropyl)(meth)acrylamide, 2-(dimethylamino)ethyl (meth)acrylate, 3-dimethylaminopropyl (meth)acrylate, hydroxyethyl (meth)acrylate, (meth)acrylonitrile, 2-hydroxy-3-(meth)acryloyloxypropyltrimethylammonium chloride, and (meth)acryloylaminoethyldimethylbenzylammonium chloride (Note that the term "(meth)acrylic acid" used herein refers to acrylic acid or methacrylic acid (this definition also applies to (meth)acrylamide and the like));
a styrene-based monomer such as styrene, a-methylstyrene, 2-methylstyrene, 3-methylstyrene, 4-methylstyrene, 4-methoxy styrene, 4-tert-butylstyrene, 4-n-butylstyrene, 4-tert-butoxystyrene, 2-hydroxymethylstyrene, 2-chlorostyrene, 4-chlorostyrene, 2,4-dichlorostyrene, 1-vinylnaphthalene, divinylbenzene, 4-styrenesulfonic acid, and an alkali metal salt (e.g., sodium salt and potassium salt) thereof; an α-olefin-based monomer such as ethylene, propene, 1-butene, 1-pentene, 1-hexene, 1-octene, and 1-decene;
a vinyl-based monomer such as 2-vinylthiophene, N-methyl-2-vinylpyrrole, 1-vinyl-2-pyrrolidone, 2-vinylpyridine, 4-vinylpyridine, N-vinylformamide, N-vinylacetamide, vinyl acetate, vinyl benzoate, methyl vinyl ketone, vinyl chloride, and vinylidene chloride;
an unsaturated carboxylic acid-based monomer such as maleic acid, fumaric acid, itaconic acid, citraconic acid, crotonic acid, and maleic anhydride;
a conjugated diene-based monomer such as 1,3-butadiene, isoprene, 2,3-dimethyl-1,3-butadiene, 2-chloro-1,3-butadiene, and 1,3-pentadiene; a non-conjugated diene-based monomer such as 4-methyl-1,4-hexadiene and 7-methyl-1,6-octadiene; and the like.

These radically polymerizable monomers may be used either alone or in combination.

The method for producing a polymer according to one embodiment of the invention can implement a controlled polymerization reaction using a wide variety of radically polymerizable monomers as compared with known atom transfer radical polymerization that utilizes an allyl halide as a polymerization initiator to introduce a carbon-carbon double bond into the polymerization-initiation terminal. Therefore, the method for producing a polymer according to one embodiment of the invention can particularly suitably be used when using a radically polymerizable monomer for which it is difficult to implement a controlled polymerization reaction using a known method. The radically polymerizable monomer that is particularly suitably used when implementing the method for producing a polymer according to one embodiment of the invention includes at least one radically polymerizable monomer selected from (meth)acrylates that include a functional group selected from a hydroxyl group, an amino group, and an ammonium group, (meth)acrylic acids, (meth)acrylamides, α-olefins, a vinyl-based monomer that includes a vinyl group that is not conjugate to an aromatic ring, and a conjugated diene-based monomer.

The amount of the organotellurium compound represented by the formula (1) and the amount of the radically polymerizable monomer may be appropriately adjusted taking account of the molecular weight and the molecular weight distribution of the desired polymer. The organotellurium compound represented by the formula (1) is normally used in an amount of 0.00005 to 0.2 mol, and preferably 0.0001 to 0.02 mol, based on 1 mol of the radically polymerizable monomer.

Radical polymerization may be effected by charging a container (in which the internal atmosphere has been replaced by an inert gas (e.g., nitrogen gas, helium gas, or argon gas) with the organotellurium compound represented by the formula (1), the radically polymerizable monomer, and an optional solvent, and stirring the mixture at a specific temperature for a specific time.

A solvent that is normally used for a radical polymerization reaction may be used as the solvent. Examples of the solvent include aromatic hydrocarbons such as benzene and toluene; ketones such as acetone and methyl ethyl ketone; esters such as ethyl acetate; ethers such as dioxane and tetrahydrofuran (THF); amides such as N,N-dimethylformamide (DMF); sulfur-containing compounds such as dimethyl sulfoxide (DMSO); alcohols such as methanol, ethanol, isopropanol, and n-butanol; halogen-containing compounds such as chloroform, carbon tetrachloride, and trifluoromethylbenzene; cellosolve and a derivative thereof such as ethyl cellosolve, butyl cellosolve, and 1-methoxy-2-propanol; water; and the like.

These solvents may be used either alone or in combination.

When using the solvent, the solvent is used in an amount of 0.01 to 50 mL, preferably 0.05 to 10 mL, and more preferably 0.1 to 5 mL, based on 1 g of the radically polymerizable monomer, for example.

The reaction temperature and the reaction time may be appropriately adjusted. The reaction temperature is normally set to 20 to 150° C., and preferably 40 to 100° C., and the reaction time is normally set to 1 minute to 100 hours, and preferably 0.1 to 30 hours.

The reaction is normally effected under normal pressure. Note that the reaction may be effected under pressure, or may be effected under reduced pressure.

When implementing the method for producing a polymer according to one embodiment of the invention, the radically polymerizable monomer may be subjected to radical polymerization in a state in which an azo-based radical generator is further present in the polymerization system.

When the polymerization reaction is effected in the presence of the azo-based radical generator, the polymerization reaction is further promoted, and a polymer can be efficiently obtained.

An arbitrary azo-based radical generator that is normally used for radical polymerization as a polymerization initiator or a polymerization promoter may be used as the azo-based radical generator.

Examples of the azo-based radical generator include 2,2'-azobis(isobutylonitrile) (AIBN),
2,2'-azobis(2-methylbutyronitrile) (AMBN),
2,2'-azobis(2,4-dimethylvaleronitrile) (ADVN),
1,1'-azobis(cyclohexane-1-carbonitrile) (ACHN),
dimethyl 2,2'-azobisisobutyrate (MAIB),
4,4'-azobis(4-cyanovaleric acid) (ACVA),
1,1'-azobis(1-acetoxy-1-phenylethane),
2,2'-azobis(2-methylbutylamide),
2,2'-azobis(4-methoxy-2,4-dimethylvaleronitrile),
2,2'-azobis(2-methylamidinopropane) dihydrochloride,
2,2'-azobis[2-(2-imidazolin-2-yl)propane],
2,2'-azobis[2-methyl-N-(2-hydroxyethyl)propionamide],
2,2'-azobis(2,4,4-trimethylpentane), 2-cyano-2-propylazoformamide,
2,2'-azobis(N-butyl-2-methylpropionamide),
2,2'-azobis(N-cyclohexyl-2-methylpropionamide), and the like.

These azo-based radical generators may be used either alone or in combination.

It is preferable to appropriately select the azo-based radical generator taking account of the reaction conditions.

For example, 2,2'-azobis(2,4-dimethylvaleronitrile) (ADVN) and 2,2'-azobis(4-methoxy-2,4-dimethylvaleronitrile) are preferable when effecting the polymerization reaction at a low temperature (40° C. or less). 2,2'-Azobis (isobutylonitrile) (AIBN), 2,2'-azobis(2-methylbutyronitrile) (AMBN), dimethyl 2,2'-azobisisobutyrate (MAIB), and 1,1'-azobis(1-acetoxy-1-phenylethane) are preferable when effecting the polymerization reaction at a medium temperature (40 to 80° C.). 1,1'-Azobis(cyclohexane-1-carbonitrile) (ACHN), 2-cyano-2-propylazoformamide, 2,2'-azobis(N-butyl-2-methylpropionamide), 2,2'-azobis(N-cyclohexyl-2-methylpropionamide), and 2,2'-azobis(2,4,4-trimethylpentane) are preferable when effecting the polymerization reaction at a high temperature (80° C. or more).

When using the azo-based radical generator, the azo-based radical generator is used in an amount of 0.01 to 100 mol, preferably 0.05 to 10 mol, and more preferably 0.05 to 2 mol, based on 1 mol of the organotellurium compound represented by the formula (1).

When implementing the method for producing a polymer according to one embodiment of the invention, the polymerization reaction may be effected in a state in which light is applied to the polymerization system (i.e., while applying light to the polymerization system).

When the polymerization reaction is effected in a state in which light is applied to the polymerization system, the polymerization reaction is further promoted, and a polymer can be efficiently obtained.

Ultraviolet rays (light having a wavelength of 200 to 380 nm) or visible light (light having a wavelength of 380 to 830 nm) is preferable as light applied to the polymerization system. Light may be applied to the polymerization system using a method that is normally used when effecting a photopolymerization reaction. For example, light may be applied to the polymerization system using a light source such as a low-pressure mercury lamp, a medium-pressure mercury lamp, a high-pressure mercury lamp, an ultra-high-pressure mercury lamp, a chemical lamp, a black light lamp, a microwave-excited mercury lamp, a metal halide lamp, a xenon lamp, a krypton lamp, or an LED lamp.

Note that the azo-based radical generator and the application of light may be used in combination. However, the polymerization reaction is normally promoted sufficiently when either the azo-based radical generator or the application of light is used.

When implementing the method for producing a polymer according to one embodiment of the invention, the radically polymerizable monomer may be subjected to radical polymerization in a state in which the ditelluride compound represented by the formula (3) is further present in the polymerization system.

When the polymerization reaction is effected in the presence of the ditelluride compound represented by the formula (3), it is possible to more advantageously control the polymerization reaction, and obtain a polymer having a molecular weight close to the theoretical value and a narrow molecular weight distribution.

Each of $R^{10}$ and $R^{11}$ in the formula (3) independently represents a group selected from an alkyl group, a substituted or unsubstituted cycloalkyl group, a substituted or unsubstituted aryl group, and a substituted or unsubstituted heteroaromatic ring group. Specific examples of the alkyl group, the substituted or unsubstituted cycloalkyl group, the substituted or unsubstituted aryl group, and the substituted or unsubstituted heteroaromatic ring group that may be represented by $R^{10}$ and $R^{11}$ include those mentioned above in connection with the alkyl group, the substituted or unsubstituted cycloalkyl group, the substituted or unsubstituted aryl group, and the substituted or unsubstituted heteroaromatic ring group that may be represented by $R^1$.

Specific examples of the ditelluride compound represented by the formula (3) include dimethyl ditelluride, diethyl ditelluride, di(n-propyl) ditelluride, diisopropyl ditelluride, dicyclopropyl ditelluride, di(n-butyl) ditelluride, di(sec-butyl) ditelluride, di(tert-butyl) ditelluride, dicyclobutyl ditelluride, diphenyl ditelluride, bis(p-methoxyphenyl) ditelluride, bis(p-aminophenyl) ditelluride, bis(p-nitrophenyl) ditelluride, bis(p-cyanophenyl) ditelluride, bis(p-sulfonylphenyl) ditelluride, bis(2-naphthyl) ditelluride, 4,4'-dypyridyl ditelluride, and the like.

These ditelluride compounds may be used either alone or in combination.

When using the ditelluride compound represented by the formula (3), the ditelluride compound represented by the formula (3) is used in an amount of 0.01 to 100 mol, preferably 0.1 to 10 mol, and more preferably 0.1 to 5 mol, based on 1 mol of the organotellurium compound represented by the formula (1), for example.

Note that the ditelluride compound represented by the formula (3) may be used in combination with the azo-based radical generator, or may be used in combination with the application of light.

After completion of the reaction, the polymer may be isolated and purified using an ordinary method. For example, the solvent and the residual radically polymerizable monomer may be evaporated from the reaction solution under reduced pressure to isolate the polymer, or the reaction solution may be poured into a poor solvent to precipitate the polymer.

The molecular weight of a polymer that is obtained by the method for producing a polymer according to one embodiment of the invention can be adjusted by adjusting the reaction time and the amount of organotellurium compound. For example, the number average molecular weight of the polymer is 500 to 1,000,000, and preferably 1,000 to 50,000. The molecular weight distribution (Mw/Mn) of the polymer is normally 1.01 to 2.50, preferably 1.01 to 2.00, more preferably 1.01 to 1.50, still more preferably 1.01 to 1.30, and most preferably 1.01 to 1.15.

The method for producing a polymer according to one embodiment of the invention can produce a copolymer when two or more radically polymerizable monomers are used.

For example, the method for producing a polymer according to one embodiment of the invention can produce a random copolymer when two or more radically polymerizable monomers are simultaneously present in the polymerization system.

The method for producing a polymer according to one embodiment of the invention can produce a block copolymer when two or more radically polymerizable monomers are sequentially reacted, since the polymerization reaction proceeds in a living manner (described later).

The growing terminal of the polymer chain during the polymerization reaction effected by the method for producing a polymer according to one embodiment of the invention is a highly reactive organotellurium site ($R^1$-Te- or $R^7$-Te-) derived from the radical polymerization initiator according to one embodiment of the invention, and has living properties.

When the growing terminal of the polymer chain that has living properties is exposed to air, the growing terminal is substituted with a hydrogen atom or a hydroxyl group, and is inactivated.

The other terminal (polymerization-initiation terminal) of the polymer obtained by the method for producing a polymer according to one embodiment of the invention is a group represented by $(R^5)(R^6)C=C(R^4)-C(R^2)(R^3)-$ that is derived from the organotellurium compound represented by the formula (1).

Therefore, the method for producing a polymer according to one embodiment of the invention can efficiently produce a polymer that includes a double bond at the molecular terminal, has a controlled molecular weight and molecular weight distribution, and is useful as a macromonomer and the like.

EXAMPLES

The invention is further described below by way of examples and the like.

Note that the invention is not limited to the following examples and the like. Note that the units "parts" and "%" respectively refer to "parts by weight" and "wt %" unless otherwise indicated.

The measurement methods used in connection with the examples are described below.

$^1$H-NMR measurement

The $^1$H-NMR measurement was performed using an NMR spectrometer "BRUKER-500" (manufactured by BRUKER) (solvent: CDCl$_3$ or d-DMSO).

Gas Chromatography Measurement

The gas chromatography measurement was performed using a gas chromatograph "GC2010" (manufactured by Shimadzu Corporation) and a column "ZB-5" (manufactured by Phenomenex). The quantitative determination was performed based on an internal standard method using mesitylene.

Gel Permeation Chromatography (GPC) Measurement

The weight average molecular weight (Mw), the number average molecular weight (Mn), and the molecular weight distribution (Mw/Mn) of the polymer were determined as polystyrene-equivalent values by gel permeation chromatography (GPC) measurement using a GPC system "HLC-8220" (manufactured by Tosoh Corporation) (column: TSK-GEL G6000HHR, G5000HHR, G4000HHR, and G2500HHR (manufactured by Tosoh Corporation) (that were sequentially connected), eluent: tetrahydrofuran (THF)).

Synthesis Example 1

A 300 mL three-necked flask was charged with 5.23 g (41 mmol) of metallic tellurium (manufactured by Aldrich (hereinafter the same)) and 45 mL of THF in a nitrogen atmosphere to prepare a suspension. The suspension was cooled to 0° C. with stirring. 45.0 mL (43.0 mmol) of methyllithium (1.10 M diethyl ether solution, manufactured by Kanto Chemical Co., Inc. (hereinafter the same)) was added dropwise to the suspension over 10 minutes while cooling the suspension with stirring. After the dropwise addition, the mixture contained in the three-necked flask was stirred at room temperature (25° C.) for 20 minutes to obtain a reaction solution in which the metallic tellurium had completely disappeared.

30 mL of a saturated NH$_4$Cl aqueous solution was added to the reaction solution with stirring, and the mixture was stirred for 1 hour in air. The organic layer was separated, and sequentially washed with water and a saturated NaCl aqueous solution. The organic layer (i.e., the reaction solution subjected to washing) was dried over anhydrous magnesium sulfate, and filtered through Celite. The filtrate was concentrated under reduced pressure, and the concentrate was subjected to vacuum distillation (0.6 mmHg, 43° C.) to obtain 2.48 g (yield: 42%) of dimethyl ditelluride as a brown oily product.

The $^1$H-NMR data of the resulting dimethyl ditelluride is shown below. $^1$H-NMR (500 MHz, CDCl$_3$, TMS, δ ppm) 2.67 (s, 6H)

Synthesis Example 2

A 300 mL three-necked flask was charged with 8.75 g (68.6 mmol) of metallic tellurium and 90 mL of THF in a nitrogen atmosphere to prepare a suspension. The suspension was cooled to 0° C. with stirring. 45.0 mL (72.0 mmol) of n-butyllithium (1.6 M hexane solution, manufactured by Kanto Chemical Co., Inc. (hereinafter the same)) was added dropwise to the suspension over 10 minutes while cooling the suspension with stirring. After the dropwise addition, the mixture contained in the three-necked flask was stirred at room temperature (25° C.) for 20 minutes to obtain a reaction solution in which the metallic tellurium had completely disappeared.

50 mL of a saturated NH$_4$Cl aqueous solution was added to the reaction solution with stirring, and the mixture was stirred for 1 hour in air. The organic layer was separated, and sequentially washed with water and a saturated NaCl aqueous solution.

The organic layer (i.e., the reaction solution subjected to washing) was dried over anhydrous magnesium sulfate, and filtered through Celite. The filtrate was concentrated under reduced pressure, and the concentrate was subjected to vacuum distillation (0.2 mmHg, 84° C.) to obtain 4.98 g (yield: 39%) of dibutyl ditelluride as a brown oily product.

The $^1$H-NMR data of the resulting dibutyl ditelluride is shown below. $^1$H-NMR (500 MHz, CDCl$_3$, TMS, δ ppm) 0.93 (t, J=7.4 Hz, 3H), 1.35-1.43 (m, 4H), 1.67-1.74 (m, 4H), 3.11 (t, J=7.4 Hz, 4H)

Example 1

A 300 mL three-necked flask was charged with 11.48 g (90 mmol) of metallic tellurium and 86 mL of THF in a nitrogen atmosphere to prepare a suspension. The suspension was cooled to 0° C. with stirring. 86.0 mL (94.5 mmol) of methyllithium (1.10 M diethyl ether solution) was added dropwise to the suspension over 10 minutes while cooling the suspension with stirring. After the dropwise addition, the mixture contained in the three-necked flask was stirred at room temperature (25° C.) for 20 minutes to obtain a reaction solution in which the metallic tellurium had completely disappeared.

The reaction solution was cooled to 0° C. with stirring. 11.4 g (94.5 mmol) of allyl bromide (manufactured by Tokyo Chemical Industry Co., Ltd. (hereinafter the same)) was added to the reaction solution while cooling the reaction solution with stirring. After reacting the mixture contained in the three-necked flask for 2 hours with stirring, the reaction solution was returned to room temperature.

The resulting reaction solution was sequentially washed with deaerated water, a deaerated saturated NH$_4$Cl aqueous solution, and a deaerated saturated NaCl aqueous solution. The organic layer (i.e., the reaction solution subjected to washing) was dried over anhydrous magnesium sulfate, and filtered through Celite in a nitrogen atmosphere.

The filtrate was concentrated under reduced pressure, and the concentrate was subjected to vacuum distillation (33 mmHg, 55° C.) to obtain 6.55 g (yield: 40%) of 3-methyltellanyl-1-propene as a yellow oily product.

The $^1$H-NMR data of the resulting 3-methyltellanyl-1-propene is shown below. $^1$H-NMR (500 MHz, CDCl$_3$, TMS, δ ppm) 1.85 (s, 3H), 3.31 (d, J=8.5 Hz, 2H), 4.80 (d, J=9.0 Hz, 1H), 4.85 (d, J=17.0 Hz, 1H), 5.90-5.99 (m, 1H)

Example 2

A 300 mL three-necked flask was charged with 6.38 g (50 mmol) of metallic tellurium and 50 mL of THF in a nitrogen atmosphere to prepare a suspension. The suspension was cooled to 0° C. with stirring. 48.6 mL (52.5 mmol) of phenyllithium (1.08 M cyclohexane-diethyl ether solution, manufactured by Kanto Chemical Co., Inc.) was added dropwise to the suspension over 10 minutes while cooling the suspension with stirring. After the dropwise addition, the mixture contained in the three-necked flask was stirred at room temperature (25° C.) for 20 minutes to obtain a reaction solution in which the metallic tellurium had completely disappeared.

The reaction solution was cooled to 0° C. with stirring. 6.35 g (52.5 mmol) of allyl bromide was added to the reaction solution while cooling the reaction solution with stirring. After reacting the mixture contained in the three-necked flask for 2 hours with stirring, the reaction solution was returned to room temperature.

The resulting reaction solution was sequentially washed with deaerated water, a deaerated saturated NH$_4$Cl aqueous solution, and a deaerated saturated NaCl aqueous solution. The organic layer (i.e., the reaction solution subjected to washing) was dried over anhydrous magnesium sulfate, and filtered through Celite in a nitrogen atmosphere. The filtrate was concentrated under reduced pressure, and the concentrate was subjected to vacuum distillation (2.0 mmHg, 70° C.) to obtain 5.6 g (yield: 46%) of 3-phenyltellanyl-1-propene as a yellow oily product.

The $^1$H-NMR data of the resulting 3-phenyltellanyl-1-propene is shown below. $^1$H-NMR (500 MHz, CDCl$_3$, δ ppm) 3.63 (dd, 2H), 4.77 (d, J=10.0 Hz, 1H), 4.83 (dd, J=16.8 Hz, 1H), 6.03-6.12 (m, 1H), 7.18-7.78 (m, 5H)

Example 3

A 300 mL three-necked flask was charged with 3.76 g (29.5 mmol) of metallic tellurium and 38 mL of THF in a nitrogen atmosphere to prepare a suspension. The suspension was cooled to 0° C. with stirring. 19.4 mL (31.0 mmol) of n-butyllithium (1.6 M hexane solution) was added dropwise to the suspension over 10 minutes while cooling the suspension with stirring. After the dropwise addition, the mixture contained in the three-necked flask was stirred at room temperature (25° C.) for 20 minutes to obtain a reaction solution in which the metallic tellurium had completely disappeared.

The reaction solution was cooled to 0° C. with stirring. 5.0 g (31.0 mmol) of 3-bromocyclohexene (manufactured by Tokyo Chemical Industry Co., Ltd.) was added to the reaction solution while cooling the reaction solution with stirring. After reacting the mixture contained in the three-necked flask for 2 hours with stirring, the reaction solution was returned to room temperature.

The resulting reaction solution was sequentially washed with deaerated water, a deaerated saturated NH$_4$Cl aqueous solution, and a deaerated saturated NaCl aqueous solution. The organic layer (i.e., the reaction solution subjected to washing) was dried over anhydrous magnesium sulfate, and filtered through Celite in a nitrogen atmosphere.

The filtrate was concentrated under reduced pressure, and the concentrate was subjected to vacuum distillation (1.0 mmHg, 82° C.) to obtain 4.47 g (yield: 57%) of 3-[(n-butyl) tellanyl]-1-cyclohexene as a yellow oily product.

The $^1$H-NMR data of the resulting 3-[(n-butyl)tellanyl]-1-cyclohexene is shown below.

$^1$H-NMR (500 MHz, CDCl$_3$, TMS, δ ppm) 0.92 (t, J=7.5 Hz, 3H), 1.38 (dt, J=7.5 Hz, 14.8 Hz, 2H), 1.64-1.89 (m, 4H), 2.01-2.22 (m, 4H), 2.62-2.78 (m, 2H), 3.96-4.00 (m, 1H), 5.56-5.60 (m, 1H), 5.85-5.89 (m, 1H)

Example 4

A 300 mL three-necked flask was charged with 3.39 g (26.6 mmol) of metallic tellurium and 25 mL of THF in a nitrogen atmosphere to prepare a suspension. The suspension was cooled to 0° C. with stirring. 25.1 mL (27.9 mmol) of methyllithium (1.11 M diethyl ether solution) was added dropwise to the suspension over 10 minutes while cooling the suspension with stirring. After the dropwise addition, the mixture contained in the three-necked flask was stirred at room temperature (25° C.) for 20 minutes to obtain a reaction solution in which the metallic tellurium had completely disappeared.

The reaction solution was cooled to 0° C. with stirring. 5.0 g (27.9 mmol) of methyl 2-(bromomethyl)acrylate (manufactured by Tokyo Chemical Industry Co., Ltd.) was added to the reaction solution while cooling the reaction solution with stirring. After reacting the mixture contained in the three-necked flask for 2 hours with stirring, the reaction solution was returned to room temperature.

The resulting reaction solution was sequentially washed with deaerated water, a deaerated saturated $NH_4Cl$ aqueous solution, and a deaerated saturated NaCl aqueous solution. The organic layer (i.e., the reaction solution subjected to washing) was dried over anhydrous magnesium sulfate, and filtered through Celite in a nitrogen atmosphere. The filtrate was concentrated under reduced pressure, and the concentrate was subjected to vacuum distillation (1.0 mmHg, 52° C.) to obtain 2.3 g (yield: 36%) of methyl 2-(methyltellanylmethyl)acrylate as a yellow oily product.

The $^1$H-NMR data of the resulting methyl 2-(methyltellanylmethyl)acrylate is shown below.

$^1$H-NMR (500 MHz, $CDCl_3$, TMS, δ ppm) 1.91 (s, 3H), 3.74 (s, 2H), 3.76 (s, 3H), 5.54 (s, 1H), 6.18 (s, 1H)

Example 5

In a glovebox in which the internal atmosphere had been replaced by nitrogen, a 30 mL glass reaction vessel was charged with 0.68 g (10 mmol) of isoprene (manufactured by Tokyo Chemical Industry Co., Ltd. (hereinafter the same)), 0.53 g (10 mmol) of acrylonitrile (manufactured by Wako Pure Chemical Industries, Ltd. (hereinafter the same)), 36.7 mg (0.20 mmol) of 3-methyltellanyl-1-propene obtained in Example 1, 5.7 mg (0.02 mmol) of dimethyl ditelluride obtained in Synthesis Example 1, 24.4 mg (0.10 mmol) of 1,1'-azobis(cyclohexane-1-carbonitrile) (manufactured by Wako Pure Chemical Industries, Ltd. (hereinafter the same)), and 0.24 g of mesitylene (manufactured by Wako Pure Chemical Industries, Ltd. (hereinafter the same)) (gas chromatography internal standard (hereinafter referred to as "internal standard")), and the mixture was stirred at 80° C. for 16 hours to effect a polymerization reaction.

The resulting polymerization reaction product was purified by evaporating a volatile component under reduced pressure, and the purified product was dried to obtain an isoprene-acrylonitrile random copolymer.

The conversion ratio of isoprene and the conversion ratio of acrylonitrile determined by gas chromatography were 93% and 84%, respectively.

The weight average molecular weight (Mw), the number average molecular weight (Mn), and the molecular weight distribution (Mw/Mn) of the isoprene-acrylonitrile random copolymer determined by GPC (with respect to a polystyrene standard sample) were 7,060, 6,130, and 1.15, respectively.

It was found by $^1$H-NMR analysis that the isoprene-acrylonitrile random copolymer included a terminal double bond in a ratio of 98%.

Example 6

A polymerization reaction was effected in the same manner as in Example 5, except that 1,1'-azobis(cyclohexane-1-carbonitrile) was not added, and light was applied to the polymerization system during the polymerization reaction using an LED lamp (output: 6 W, 5% ND filter was used), to obtain an isoprene-acrylonitrile random copolymer.

The conversion ratio of isoprene and the conversion ratio of acrylonitrile determined by gas chromatography were 88% and 81%, respectively.

The weight average molecular weight (Mw), the number average molecular weight (Mn), and the molecular weight distribution (Mw/Mn) of the isoprene-acrylonitrile random copolymer determined by GPC (with respect to a polystyrene standard sample) were 6,730, 6,100, and 1.09, respectively.

It was found by $^1$H-NMR analysis that the isoprene-acrylonitrile random copolymer included a terminal double bond in a ratio of 96%.

Example 7

A polymerization reaction was effected in the same manner as in Example 5, except that dimethyl ditelluride was not added, to obtain an isoprene-acrylonitrile random copolymer.

The conversion ratio of isoprene and the conversion ratio of acrylonitrile determined by gas chromatography were 92% and 82%, respectively.

The weight average molecular weight (Mw), the number average molecular weight (Mn), and the molecular weight distribution (Mw/Mn) of the isoprene-acrylonitrile random copolymer determined by GPC (with respect to a polystyrene standard sample) were 8,690, 6,980, and 1.25, respectively.

It was found by $^1$H-NMR analysis that the isoprene-acrylonitrile random copolymer included a terminal double bond in a ratio of 98%.

Example 8

A polymerization reaction was effected in the same manner as in Example 5, except that dimethyl ditelluride and 1,1'-azobis(cyclohexane-1-carbonitrile) were not added, and the polymerization reaction time was changed to 72 hours, to obtain an isoprene-acrylonitrile random copolymer.

The conversion ratio of isoprene and the conversion ratio of acrylonitrile determined by gas chromatography were 75% and 63%, respectively.

The weight average molecular weight (Mw), the number average molecular weight (Mn), and the molecular weight distribution (Mw/Mn) of the isoprene-acrylonitrile random copolymer determined by GPC (with respect to a polystyrene standard sample) were 4,160, 3,080, and 1.35, respectively.

It was found by $^1$H-NMR analysis that the isoprene-acrylonitrile random copolymer included a terminal double bond in a ratio of 97%.

Example 9

In a glovebox in which the internal atmosphere had been replaced by nitrogen, a 30 mL glass reaction vessel was charged with 2.56 g (20 mmol) of n-butyl acrylate (manufactured by Wako Pure Chemical Industries, Ltd. (hereinafter the same)), 36.7 mg (0.20 mmol) of 3-methyltellanyl-1-propene obtained in Example 1, 16.4 mg (0.10 mmol) of azobisisobutyronitrile (manufactured by Wako Pure Chemical Industries, Ltd. (hereinafter the same)), and 0.24 g of mesitylene (internal standard), and the mixture was stirred at 60° C. for 1 hour to effect a polymerization reaction.

The resulting polymerization reaction product was purified by evaporating a volatile component under reduced pressure, and the purified product was dried to obtain an n-butyl acrylate polymer.

The conversion ratio of n-butyl acrylate determined by gas chromatography was 91%.

The weight average molecular weight (Mw), the number average molecular weight (Mn), and the molecular weight distribution (Mw/Mn) of the n-butyl acrylate polymer determined by GPC (with respect to a polystyrene standard sample) were 18,970, 15,240, and 1.25, respectively.

It was found by $^1$H-NMR analysis that the n-butyl acrylate polymer included a terminal double bond in a ratio of 90%.

Example 10

In a glovebox in which the internal atmosphere had been replaced by nitrogen, a 30 mL glass reaction vessel was charged with 2.56 g (20 mmol) of n-butyl acrylate, 36.7 mg (0.20 mmol) of 3-methyltellanyl-1-propene obtained in Example 1, 16.4 mg (0.10 mmol) of azobisisobutyronitrile, and 0.24 g of mesitylene (internal standard), and the mixture was stirred at 60° C. for 1 hour to effect a polymerization reaction. After the addition of 1.00 g (10 mmol) of methyl methacrylate (manufactured by Wako Pure Chemical Industries, Ltd. (hereinafter the same)) and 28.5 mg (0.1 mmol) of dimethyl ditelluride obtained in Synthesis Example 1 to the reaction vessel, the mixture was stirred at 80° C. for 15 hours to effect a polymerization reaction.

The resulting polymerization reaction product was purified by evaporating a volatile component under reduced pressure, and the purified product was dried to obtain an n-butyl acrylate-methyl methacrylate block copolymer.

The conversion ratio of methyl methacrylate determined by gas chromatography was 100%.

The weight average molecular weight (Mw), the number average molecular weight (Mn), and the molecular weight distribution (Mw/Mn) of the n-butyl acrylate-methyl methacrylate block copolymer determined by GPC (with respect to a polystyrene standard sample) were 50,900, 29,600, and 1.71, respectively.

It was found by $^1$H-NMR analysis that the n-butyl acrylate-methyl methacrylate block copolymer included a terminal double bond in a ratio of 88%.

Example 11

A polymerization reaction was effected in the same manner as in Example 9, except that 2.08 g (20 mmol) of styrene (manufactured by Tokyo Chemical Industry Co., Ltd. (hereinafter the same)) was used instead of n-butyl acrylate, to obtain a styrene polymer.

The conversion ratio of styrene determined by gas chromatography was 91%.

The weight average molecular weight (Mw), the number average molecular weight (Mn), and the molecular weight distribution (Mw/Mn) of the styrene polymer determined by GPC (with respect to a polystyrene standard sample) were 10,860, 8,150, and 1.33, respectively.

It was found by $^1$H-NMR analysis that the styrene polymer included a terminal double bond in a ratio of 97%.

Example 12

In a glovebox in which the internal atmosphere had been replaced by nitrogen, a 30 mL glass reaction vessel was charged with 2.08 g (20 mmol) of styrene, 36.7 mg (0.20 mmol) of 3-methyltellanyl-1-propene obtained in Example 1, 16.4 mg (0.10 mmol) of azobisisobutyronitrile, and 0.24 g of mesitylene (internal standard), and the mixture was stirred at 60° C. for 1 hour to effect a polymerization reaction. After the addition of 1.00 g (10 mmol) of methyl methacrylate and 28.5 mg (0.1 mmol) of dimethyl ditelluride obtained in Synthesis Example 1 to the reaction vessel, the mixture was stirred at 80° C. for 15 hours to effect a polymerization reaction.

The resulting polymerization reaction product was purified by evaporating a volatile component under reduced pressure, and the purified product was dried to obtain a styrene-methyl methacrylate block copolymer.

The conversion ratio of methyl methacrylate determined by gas chromatography was 100%.

The weight average molecular weight (Mw), the number average molecular weight (Mn), and the molecular weight distribution (Mw/Mn) of the styrene-methyl methacrylate block copolymer determined by GPC (with respect to a polystyrene standard sample) were 26,600, 18,800, and 1.41, respectively.

It was found by $^1$H-NMR analysis that the styrene-methyl methacrylate block copolymer included a terminal double bond in a ratio of 92%.

Example 13

A polymerization reaction was effected in the same manner as in Example 5, except that 1.00 g (10 mmol) of methyl methacrylate was used instead of acrylonitrile, to obtain an isoprene-methyl methacrylate random copolymer.

The conversion ratio of isoprene and the conversion ratio of methyl methacrylate determined by gas chromatography were 97% and 90%, respectively.

The weight average molecular weight (Mw), the number average molecular weight (Mn), and the molecular weight distribution (Mw/Mn) of the isoprene-methyl methacrylate random copolymer determined by GPC (with respect to a polystyrene standard sample) were 9,110, 7,530, and 1.21, respectively.

It was found by $^1$H-NMR analysis that the isoprene-methyl methacrylate random copolymer included a terminal double bond in a ratio of 96%.

Example 14

A polymerization reaction was effected in the same manner as in Example 5, except that 1.28 g (10 mmol) of n-butyl acrylate was used instead of acrylonitrile, to obtain an isoprene-n-butyl acrylate random copolymer.

The conversion ratio of isoprene and the conversion ratio of n-butyl acrylate determined by gas chromatography were 99% and 87%, respectively.

The weight average molecular weight (Mw), the number average molecular weight (Mn), and the molecular weight distribution (Mw/Mn) of the isoprene-n-butyl acrylate random copolymer determined by GPC (with respect to a polystyrene standard sample) were 5,800, 4,700, and 1.23, respectively.

It was found by $^1$H-NMR analysis that the isoprene-n-butyl acrylate random copolymer included a terminal double bond in a ratio of 95%.

Example 15

A polymerization reaction was effected in the same manner as in Example 5, except that 1.04 g (10 mmol) of styrene was used instead of acrylonitrile, to obtain an isoprene-styrene random copolymer.

The conversion ratio of isoprene and the conversion ratio of styrene determined by gas chromatography were 93% and 73%, respectively.

The weight average molecular weight (Mw), the number average molecular weight (Mn), and the molecular weight distribution (Mw/Mn) of the isoprene-styrene random copolymer determined by GPC (with respect to a polystyrene standard sample) were 8,070, 6,580, and 1.19, respectively.

It was found by $^1$H-NMR analysis that the isoprene-styrene random copolymer included a terminal double bond in a ratio of 98%.

Example 16

In a glovebox in which the internal atmosphere had been replaced by nitrogen, a 30 mL stainless steel autoclave was charged with 1.62 g (30 mmol) of 1,3-butadiene (manufactured by Tokyo Chemical Industry Co., Ltd.), 1.59 g (30 mmol) of acrylonitrile, 0.6 mg (0.003 mmol) of 3-methyltellanyl-1-propene obtained in Example 1, 0.1 mg (0.0006 mmol) of dimethyl ditelluride, 1.5 mg (0.009 mmol) of 1,1'-azobis(cyclohexane-1-carbonitrile), and 0.24 g of mesitylene (internal standard), and the mixture was stirred at 80° C. for 21 hours to effect a polymerization reaction.

The resulting polymerization reaction product was purified by evaporating a volatile component under reduced pressure, and the purified product was dried to obtain a butadiene-acrylonitrile random copolymer.

The conversion ratio of 1,3-butadiene and the conversion ratio of acrylonitrile determined by gas chromatography were 81% and 58%, respectively.

The weight average molecular weight (Mw), the number average molecular weight (Mn), and the molecular weight distribution (Mw/Mn) of the butadiene-acrylonitrile random copolymer determined by GPC (with respect to a polystyrene standard sample) were 332,300, 223,000, and 1.49, respectively.

It was found by $^1$H-NMR analysis that the butadiene-acrylonitrile random copolymer included a terminal double bond in a ratio of 96%.

Example 17

In a glovebox in which the internal atmosphere had been replaced by nitrogen, a 30 mL glass reaction vessel was charged with 0.68 g (10 mmol) of cis-1,3-pentadiene (manufactured by Tokyo Chemical Industry Co., Ltd.), 0.53 g (10 mmol) of acrylonitrile, 1.2 mg (0.0067 mmol) of 3-methyltellanyl-1-propene obtained in Example 1, 0.4 mg (0.0013 mmol) of dimethyl ditelluride, 0.8 mg (0.003 mmol) of 1,1'-azobis(cyclohexane-1-carbonitrile), and 0.24 g of mesitylene (internal standard), and the mixture was stirred at 80° C. for 38 hours to effect a polymerization reaction.

The resulting polymerization reaction product was purified by evaporating a volatile component under reduced pressure, and the purified product was dried to obtain a cis-1,3-pentadiene-acrylonitrile random copolymer.

The conversion ratio of cis-1,3-pentadiene and the conversion ratio of acrylonitrile determined by gas chromatography were 76% and 36%, respectively.

The weight average molecular weight (Mw), the number average molecular weight (Mn), and the molecular weight distribution (Mw/Mn) of the cis-1,3-pentadiene-acrylonitrile random copolymer determined by GPC (with respect to a polystyrene standard sample) were 89,400, 60,400, and 1.48, respectively.

It was found by $^1$H-NMR analysis that the cis-1,3-pentadiene-acrylonitrile random copolymer included a terminal double bond in a ratio of 92%.

Example 18

A polymerization reaction was effected in the same manner as in Example 5, except that 49.1 mg (0.2 mmol) of 3-phenyltellanyl-1-propene obtained in Example 2 was used instead of 3-methyltellanyl-1-propene, and 8.2 mg (0.02 mmol) of diphenyl ditelluride (manufactured by Aldrich) was used instead of dimethyl ditelluride, to obtain an isoprene-acrylonitrile random copolymer.

The conversion ratio of isoprene and the conversion ratio of acrylonitrile determined by gas chromatography were 91% and 82%, respectively.

The weight average molecular weight (Mw), the number average molecular weight (Mn), and the molecular weight distribution (Mw/Mn) of the isoprene-acrylonitrile random copolymer determined by GPC (with respect to a polystyrene standard sample) were 5,740, 5,010, and 1.15, respectively.

It was found by $^1$H-NMR analysis that the isoprene-acrylonitrile random copolymer included a terminal double bond in a ratio of 94%.

Example 19

A polymerization reaction was effected in the same manner as in Example 5, except that 52.9 mg (0.2 mmol) of 3-[(n-butyl)tellanyl]-1-cyclohexene obtained in Example 3 was used instead of 3-methyltellanyl-1-propene, and 7.5 mg (0.02 mmol) of dibutyl ditelluride obtained in Synthesis Example 2 was used instead of dimethyl ditelluride, to obtain an isoprene-acrylonitrile random copolymer.

The conversion ratio of isoprene and the conversion ratio of acrylonitrile determined by gas chromatography were 91% and 84%, respectively.

The weight average molecular weight (Mw), the number average molecular weight (Mn), and the molecular weight distribution (Mw/Mn) of the isoprene-acrylonitrile random copolymer determined by GPC (with respect to a polystyrene standard sample) were 7,770, 6,150, and 1.26, respectively.

It was found by $^1$H-NMR analysis that the isoprene-acrylonitrile random copolymer included a terminal double bond in a ratio of 99%.

Example 20

A polymerization reaction was effected in the same manner as in Example 10, except that 48.3 mg (0.2 mmol) of methyl 2-(methyltellanylmethyl)acrylate obtained in Example 4 was used instead of 3-methyltellanyl-1-propene, to obtain an isoprene-acrylonitrile random copolymer.

The conversion ratio of isoprene and the conversion ratio of acrylonitrile determined by gas chromatography were 86% and 76%, respectively.

The weight average molecular weight (Mw), the number average molecular weight (Mn), and the molecular weight distribution (Mw/Mn) of the isoprene-acrylonitrile random copolymer determined by GPC (with respect to a polystyrene standard sample) were 8,190, 5,570, and 1.47, respectively.

It was found by $^1$H-NMR analysis that the isoprene-acrylonitrile random copolymer included a terminal double bond in a ratio of 85%.

Example 21

A polymerization reaction was effected in the same manner as in Example 9, except that 3.14 g (20 mmol) of 2-(dimethylamino)ethyl methacrylate was used instead of n-butyl acrylate, to obtain a 2-(dimethylamino)ethyl methacrylate polymer.

The conversion ratio of 2-(dimethylamino)ethyl methacrylate determined by gas chromatography was 83%. The weight average molecular weight (Mw), the number average molecular weight (Mn), and the molecular weight distribution (Mw/Mn) of the 2-(dimethylamino)ethyl methacrylate polymer determined by GPC (with respect to a polystyrene standard sample) were 25,900, 19,300, and 1.34, respectively.

It was found by $^1$H-NMR analysis that the 2-(dimethylamino)ethyl methacrylate polymer included a terminal double bond in a ratio of 87%.

Comparative Example 1

In a glovebox in which the internal atmosphere had been replaced by nitrogen, a 30 mL glass reaction vessel was charged with 28.7 mg (0.2 mmol) of copper(I) bromide (manufactured by Wako Pure Chemical Industries, Ltd. (hereinafter the same)), 34.7 mg (0.2 mmol) of N,N,N',N'',N''-pentamethyldiethylenetriamine (manufactured by Wako Pure Chemical Industries, Ltd.), 0.68 g (10 mmol) of isoprene, 0.53 g (10 mmol) of acrylonitrile, 24.2 mg (0.20 mmol) of allyl bromide, and 0.24 g of mesitylene (internal standard), and the mixture was stirred at 80° C. for 15 hours to effect a polymerization reaction.

The resulting polymerization reaction product was purified by evaporating a volatile component under reduced pressure, and the purified product was dried.

The conversion ratio of isoprene and the conversion ratio of acrylonitrile determined by gas chromatography were 21% and 27%, respectively.

The weight average molecular weight (Mw), the number average molecular weight (Mn), and the molecular weight distribution (Mw/Mn) of the resulting product determined by GPC (with respect to a polystyrene standard sample) were 370, 360, and 1.04, respectively. It was thus found that an oligomer was obtained by the polymerization reaction.

Comparative Example 2

In a glovebox in which the internal atmosphere had been replaced by nitrogen, a 30 mL glass reaction vessel was charged with 28.7 mg (0.2 mmol) of copper(I) bromide, 34.7 mg (0.2 mmol) of N,N,N',N'',N''-pentamethyldiethylenetriamine, 2 mL of toluene, 3.14 g (20 mmol) of 2-(dimethylamino)ethyl methacrylate, 24.2 mg (0.20 mmol) of allyl bromide, and 0.24 g of mesitylene (internal standard), and the mixture was stirred at 80° C. for 15 hours to effect a polymerization reaction.

The resulting polymerization reaction product was purified by evaporating a volatile component under reduced pressure, and the purified product was dried to obtain a 2-(dimethylamino)ethyl methacrylate polymer.

The conversion ratio of 2-(dimethylamino)ethyl methacrylate determined by gas chromatography was 42%.

The weight average molecular weight (Mw), the number average molecular weight (Mn), and the molecular weight distribution (Mw/Mn) of the 2-(dimethylamino)ethyl methacrylate polymer determined by GPC (with respect to a polystyrene standard sample) were 36,000, 13,300, and 2.71, respectively. Specifically, the 2-(dimethylamino)ethyl methacrylate polymer had a relatively wide molecular weight distribution.

The invention claimed is:

1. A method for producing a polymer comprising subjecting a radically polymerizable monomer to radical polymerization in a state in which a radical polymerization initiator is present in a polymerization system,
    wherein the radical polymerization initiator is an organotellurium compound represented by the following formula (1),

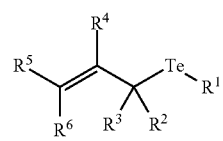

(1)

wherein $R^1$ represents a group selected from:
   an alkyl group having 1 to 10 carbon atoms;
   a cycloalkyl group having 3 to 10 carbon atoms which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms);
   an aryl group having 6 to 20 carbon atoms which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms); and
   an aromatic heterocyclic group which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 20 carbon atoms, an alkoxy group having 1 to 8 carbon atoms, an aryloxy group having 6 to 10 carbon atoms, or a haloalkyl group having 1 to 8 carbon atoms),
   each of $R^2$ and $R^3$ independently represents a group selected from:
   a hydrogen atom;
   an aliphatic hydrocarbon group having 1 to 10 carbon atoms;
   an aryl group having 6 to 20 carbon atoms which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms);

an aromatic heterocyclic group which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms or a haloalkyl group having 1 to 8 carbon atoms);

a halogen atom;

a carboxyl group;

a hydrocarbyl oxycarbonyl group having 2 to 10 carbon atoms;

a cyano group; and an amide group, and each of $R^4$, $R^5$ and $R^6$ independently represents a group selected from:

a hydrogen atom;

an aliphatic hydrocarbon group having 1 to 10 carbon atoms;

an aryl group having 6 to 20 carbon atoms which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms);

an aromatic heterocyclic group which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms);

a halogen atom;

a carboxyl group;

a hydrocarbyl oxycarbonyl group having 2 to 10 carbon atoms;

a cyano group; and an amide group, and a group represented by the following formula (2), wherein 2 groups selected from $R^2$ to $R^6$ may bond together to form a ring other than an aromatic ring,

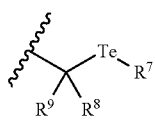

(2)

wherein $R^7$ represents a group selected from:

an alkyl group having 1 to 10 carbon atoms;

a cycloalkyl group having 3 to 10 carbon atoms which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms);

an aryl group having 6 to 20 carbon atoms which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms); and an aromatic heterocyclic group which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 20 carbon atoms, an alkoxy group having 1 to 8 carbon atoms, an aryloxy group having 6 to 10 carbon atoms, or a haloalkyl group having 1 to 8 carbon atoms), and each of $R^8$ and $R^9$ independently represents a group selected from:

a hydrogen atom;

an aliphatic hydrocarbon group having 1 to 10 carbon atoms;

an aryl group having 6 to 20 carbon atoms which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms);

an aromatic heterocyclic group which is unsubstituted, or substituted with a substituent selected from a halogen atom, an alkyl group having 1 to 8 carbon atoms, an alkoxy group having 1 to 8 carbon atoms, an amino group, a nitro group, a cyano group, and —CORa (wherein Ra represents an alkyl group having 1 to 8 carbon atoms, a cycloalkyl group having 3 to 8 carbon atoms, an aryl group having 6 to 10 carbon atoms, an alkoxy group having 1 to 8 carbon atoms, an aryloxy group having 6 to 10 carbon atoms, or a haloalkyl group having 1 to 8 carbon atoms);

a halogen atom;

a carboxyl group;

a hydrocarbyl oxycarbonyl group having 2 to 10 carbon atoms;

a cyano group; and an amide group, wherein the wavy line represents a bond with the carbon atoms constituting the double bond in formula (1), wherein one of the terminal of the polymer produced is a group represented by $(R^5)(R^6)C=C(R^4)-C(R^2)(R^3)-$ that is derived from the organotellurium compound.

2. The method for producing a polymer according to claim 1, wherein the radically polymerizable monomer is subjected to radical polymerization in a state in which an azo-based radical generator is further present in the polymerization system.

3. The method for producing a polymer according to claim 1, wherein the radically polymerizable monomer is subjected to radical polymerization in a state in which light having a wavelength of 200 to 380 nm is applied to the polymerization system.

4. The method for producing a polymer according to claim 1, wherein the radically polymerizable monomer is subjected to radical polymerization in a state in which a ditelluride compound represented by a formula (3) is further present in the polymerization system, $$R^{10}Te-TeR^{11} \tag{3}$$

wherein each of $R^{10}$ and $R^{11}$ independently represents a group selected from an alkyl group, a substituted or unsubstituted cycloalkyl group, a substituted or unsubstituted aryl group, and a substituted or unsubstituted heteroaromatic ring group.

5. The method for producing a polymer according to claim 1, wherein the molecular weight distribution of the polymer produced is 1.01 to 2.50.

* * * * *